US008884184B2

(12) United States Patent
Gaudiosi et al.

(10) Patent No.: US 8,884,184 B2
(45) Date of Patent: Nov. 11, 2014

(54) POLYMER TUBING LASER MICROMACHINING

(75) Inventors: David Gaudiosi, Rohnert Park, CA (US); Michael Greenberg, Santa Rosa, CA (US); Michael Mielke, Santa Rosa, CA (US); Tim Booth, Penngrove, CA (US); Gordon Masor, Petaluma, CA (US)

(73) Assignee: Raydiance, Inc., Petaluma, CA (US)

( * ) Notice: Subject to any disclaimer, the term of this patent is extended or adjusted under 35 U.S.C. 154(b) by 303 days.

(21) Appl. No.: 13/208,259

(22) Filed: Aug. 11, 2011

(65) Prior Publication Data

US 2012/0037609 A1    Feb. 16, 2012

Related U.S. Application Data

(60) Provisional application No. 61/373,201, filed on Aug. 12, 2010.

(51) Int. Cl.
*B23K 26/38* (2014.01)
*B23K 26/40* (2014.01)
*A61F 2/91* (2013.01)

(52) U.S. Cl.
CPC .............. *B23K 26/4065* (2013.01); *A61F 2/91* (2013.01)
USPC .............. 219/121.67; 219/121.7; 219/121.61; 219/121.82; 623/1.49; 623/1.15

(58) Field of Classification Search
CPC ......... B23K 26/00; B23K 26/38; B65G 47/24

USPC .............. 219/121.67–121.7, 121.82, 121.84; 623/1.13–1.15, 1.17, 1.49, 1.42

See application file for complete search history.

(56) References Cited

U.S. PATENT DOCUMENTS 3,654,624 A    4/1972  Becker et al.
3,764,641 A    10/1973 Ash (Continued)

FOREIGN PATENT DOCUMENTS

DE    WO2007000194 A1    4/2007
EP        0214100        3/1987

(Continued)

OTHER PUBLICATIONS

Agostinelli, J. et al., "Optical Pulse Shaping with a Grating Pair," Applied Optics, vol. 18, No. 14, pp. 2500-2504, Jul. 15, 1979.

(Continued)

*Primary Examiner* — Mark Paschall
(74) *Attorney, Agent, or Firm* — Haverstock & Owens LLP

(57) ABSTRACT

An apparatus for athermal ablation of a workpiece. The apparatus may include a laser device to direct a laser beam at the workpiece to remove a plurality of sections from the workpiece by athermal ablation. The removal may occur in a plurality of discrete motions that cause the laser beam to trace along outer perimeters of the sections in a specific order maintaining mechanical stability of the plurality of sections. The apparatus may further include a process gas nozzle to deliver process gas coaxially with the laser beam to clear debris and cool the workpiece, and a workpiece holder to hold and maneuver the workpiece during the removal of the plurality of sections.

21 Claims, 8 Drawing Sheets

(56) References Cited

U.S. PATENT DOCUMENTS

| | | | |
|---|---|---|---|
| 3,963,953 A | 6/1976 | Thornton, Jr. | |
| 4,449,215 A | 5/1984 | Reno | |
| 4,590,598 A | 5/1986 | O'Harra, II | |
| 4,622,095 A | 11/1986 | Grobman et al. | |
| 4,673,795 A | 6/1987 | Ortiz, Jr. | |
| 4,718,418 A | 1/1988 | L'Esperance, Jr. | |
| 4,743,769 A | 5/1988 | Schwaiger et al. | |
| 4,878,127 A * | 10/1989 | Zollman et al. | 358/3.32 |
| 4,907,586 A | 3/1990 | Bille et al. | |
| 4,915,757 A | 4/1990 | Rando | |
| 4,988,348 A | 1/1991 | Bille | |
| 4,994,059 A | 2/1991 | Kosa et al. | |
| 5,014,290 A | 5/1991 | Moore et al. | |
| 5,053,171 A | 10/1991 | Portney et al. | |
| 5,098,426 A | 3/1992 | Sklar et al. | |
| 5,122,439 A | 6/1992 | Miersch et al. | |
| 5,146,088 A | 9/1992 | Kingham et al. | |
| 5,162,643 A | 11/1992 | Currie | |
| 5,194,713 A | 3/1993 | Egitto et al. | |
| 5,217,003 A | 6/1993 | Wilk | |
| 5,265,107 A | 11/1993 | Delfyett, Jr. | |
| 5,293,186 A | 3/1994 | Seden et al. | |
| 5,302,835 A | 4/1994 | Bendett et al. | |
| 5,331,131 A | 7/1994 | Opdyke | |
| 5,409,376 A | 4/1995 | Murphy | |
| 5,411,918 A | 5/1995 | Keible et al. | |
| 5,418,809 A | 5/1995 | August, Jr. et al. | |
| 5,520,679 A | 5/1996 | Lin | |
| 5,533,139 A | 7/1996 | Parker et al. | |
| 5,548,098 A | 8/1996 | Sugawara et al. | |
| 5,624,587 A | 4/1997 | Otsuki et al. | |
| 5,656,186 A | 8/1997 | Mourou et al. | |
| 5,666,722 A | 9/1997 | Tamm et al. | |
| 5,670,067 A | 9/1997 | Koide et al. | |
| 5,720,894 A | 2/1998 | Neev et al. | |
| 5,736,709 A | 4/1998 | Neiheisel | |
| 5,781,289 A | 7/1998 | Sabsabi et al. | |
| 5,786,117 A | 7/1998 | Hoshi et al. | |
| 5,788,688 A | 8/1998 | Bauer et al. | |
| 5,790,574 A | 8/1998 | Rieger et al. | |
| 5,841,099 A | 11/1998 | Owen et al. | |
| 5,844,149 A | 12/1998 | Akiyoshi et al. | |
| 5,847,825 A | 12/1998 | Alexander | |
| 5,862,845 A | 1/1999 | Chin et al. | |
| 5,875,408 A | 2/1999 | Bendett et al. | |
| 5,898,485 A | 4/1999 | Nati, Jr. | |
| 5,903,662 A | 5/1999 | DeCarlo | |
| 5,907,157 A | 5/1999 | Yoshioka et al. | |
| 5,994,667 A * | 11/1999 | Merdan et al. | 219/121.67 |
| 5,999,847 A | 12/1999 | Elstrom | |
| 6,016,452 A | 1/2000 | Kasevich | |
| 6,020,591 A | 2/2000 | Harter et al. | |
| 6,071,276 A | 6/2000 | Abela | |
| 6,099,522 A | 8/2000 | Knopp et al. | |
| 6,120,857 A | 9/2000 | Balooch et al. | |
| 6,156,030 A | 12/2000 | Neev | |
| 6,161,543 A | 12/2000 | Cox et al. | |
| 6,190,380 B1 | 2/2001 | Abela | |
| 6,211,485 B1 | 4/2001 | Burgess | |
| 6,228,748 B1 | 5/2001 | Anderson et al. | |
| 6,275,250 B1 | 8/2001 | Sanders et al. | |
| 6,325,792 B1 | 12/2001 | Swinger et al. | |
| 6,327,074 B1 | 12/2001 | Bass et al. | |
| 6,340,806 B1 | 1/2002 | Smart et al. | |
| RE37,585 E | 3/2002 | Mourou et al. | |
| 6,355,908 B1 | 3/2002 | Tatah et al. | |
| 6,362,454 B1 | 3/2002 | Liu | |
| 6,365,869 B1 | 4/2002 | Swain et al. | |
| 6,370,171 B1 | 4/2002 | Horn et al. | |
| 6,371,469 B1 | 4/2002 | Gray | |
| 6,407,363 B2 | 6/2002 | Dunsky et al. | |
| 6,425,912 B1 | 7/2002 | Knowlton | |
| 6,433,301 B1 | 8/2002 | Dunsky et al. | |
| 6,433,303 B1 | 8/2002 | Liu et al. | |
| 6,433,305 B1 | 8/2002 | Liu et al. | |
| 6,437,283 B1 | 8/2002 | Wiggermann et al. | |
| 6,463,314 B1 | 10/2002 | Haruna | |
| 6,482,199 B1 | 11/2002 | Neev | |
| 6,485,413 B1 | 11/2002 | Boppart et al. | |
| 6,486,435 B1 | 11/2002 | Beyer et al. | |
| 6,496,099 B2 | 12/2002 | Wang et al. | |
| 6,526,327 B2 | 2/2003 | Kar et al. | |
| 6,541,731 B2 | 4/2003 | Mead et al. | |
| 6,552,301 B2 | 4/2003 | Herman et al. | |
| 6,555,781 B2 * | 4/2003 | Ngoi et al. | 219/121.67 |
| 6,562,698 B2 | 5/2003 | Manor | |
| 6,574,024 B1 | 6/2003 | Liu | |
| 6,574,250 B2 | 6/2003 | Sun et al. | |
| 6,583,381 B1 | 6/2003 | Duignan | |
| 6,592,574 B1 | 7/2003 | Shimmick et al. | |
| 6,593,753 B2 | 7/2003 | Scott et al. | |
| 6,621,040 B1 | 9/2003 | Perry et al. | |
| 6,621,045 B1 | 9/2003 | Liu et al. | |
| 6,627,421 B1 | 9/2003 | Unger et al. | |
| 6,627,844 B2 | 9/2003 | Liu et al. | |
| 6,642,477 B1 | 11/2003 | Patel et al. | |
| 6,661,568 B2 | 12/2003 | Hollemann et al. | |
| 6,677,552 B1 | 1/2004 | Tulloch et al. | |
| 6,681,079 B1 | 1/2004 | Maroney | |
| 6,695,835 B2 | 2/2004 | Furuno et al. | |
| 6,696,008 B2 * | 2/2004 | Brandinger | 264/400 |
| 6,697,408 B2 | 2/2004 | Kennedy et al. | |
| 6,700,094 B1 | 3/2004 | Kuntze | |
| 6,706,036 B2 | 3/2004 | Lai | |
| 6,710,288 B2 | 3/2004 | Liu et al. | |
| 6,710,293 B2 | 3/2004 | Liu et al. | |
| 6,720,519 B2 | 4/2004 | Liu et al. | |
| 6,727,458 B2 | 4/2004 | Smart | |
| 6,738,144 B1 | 5/2004 | Dogariu | |
| 6,744,552 B2 | 6/2004 | Scalora et al. | |
| 6,749,285 B2 | 6/2004 | Liu et al. | |
| 6,785,445 B2 | 8/2004 | Kuroda et al. | |
| 6,787,733 B2 | 9/2004 | Lubatschowski et al. | |
| 6,787,734 B2 | 9/2004 | Liu | |
| 6,791,060 B2 | 9/2004 | Dunsky et al. | |
| 6,791,071 B2 | 9/2004 | Woo et al. | |
| 6,795,461 B1 | 9/2004 | Blair et al. | |
| 6,803,539 B2 | 10/2004 | Liu et al. | |
| 6,804,574 B2 | 10/2004 | Liu et al. | |
| 6,822,187 B1 | 11/2004 | Hermann et al. | |
| 6,822,251 B1 | 11/2004 | Arenberg et al. | |
| 6,824,540 B1 | 11/2004 | Lin | |
| 6,829,517 B2 | 12/2004 | Cheng et al. | |
| 6,836,703 B2 | 12/2004 | Wang et al. | |
| 6,878,900 B2 | 4/2005 | Corkum et al. | |
| 6,887,804 B2 | 5/2005 | Sun et al. | |
| 6,897,405 B2 | 5/2005 | Cheng et al. | |
| 6,902,561 B2 | 6/2005 | Kurtz et al. | |
| 6,915,040 B2 | 7/2005 | Willner et al. | |
| 6,943,359 B2 | 9/2005 | Vardeny et al. | |
| 6,994,703 B2 | 2/2006 | Wang et al. | |
| 7,001,373 B2 | 2/2006 | Clapham et al. | |
| 7,022,119 B2 | 4/2006 | Hohla | |
| 7,097,640 B2 | 8/2006 | Wang et al. | |
| 7,132,289 B2 | 11/2006 | Kobayashi et al. | |
| 7,143,769 B2 | 12/2006 | Stoltz et al. | |
| 7,217,266 B2 | 5/2007 | Anderson et al. | |
| 7,220,255 B2 | 5/2007 | Lai | |
| 7,349,589 B2 | 3/2008 | Temelkuran et al. | |
| 7,361,171 B2 | 4/2008 | Stoltz et al. | |
| 7,367,969 B2 | 5/2008 | Stoltz et al. | |
| 7,413,565 B2 | 8/2008 | Wang et al. | |
| 7,414,780 B2 | 8/2008 | Fermann et al. | |
| 7,674,719 B2 | 3/2010 | Li et al. | |
| 7,675,674 B2 | 3/2010 | Bullington et al. | |
| 7,751,118 B1 | 7/2010 | Di Teodoro et al. | |
| 7,759,607 B2 | 7/2010 | Chism, II | |
| 7,773,216 B2 | 8/2010 | Cheng et al. | |
| 7,792,408 B2 | 9/2010 | Varming | |
| 7,943,533 B2 | 5/2011 | Mizuno | |
| 7,998,404 B2 * | 8/2011 | Huang et al. | 422/22 |
| RE43,605 E * | 8/2012 | O'Brien et al. | 264/400 |
| 8,338,746 B2 | 12/2012 | Sun et al. | |
| 8,373,090 B2 * | 2/2013 | Gale et al. | 219/121.67 |

(56) References Cited

U.S. PATENT DOCUMENTS

| | | |
|---|---|---|
| 2001/0009250 A1 | 7/2001 | Herman et al. |
| 2001/0021294 A1 | 9/2001 | Cai et al. |
| 2002/0003130 A1 | 1/2002 | Sun et al. |
| 2002/0095142 A1 | 7/2002 | Ming |
| 2002/0115273 A1 | 8/2002 | Chandra et al. |
| 2002/0153500 A1 | 10/2002 | Fordahl et al. |
| 2003/0031410 A1 | 2/2003 | Schnitzer |
| 2003/0055413 A1 | 3/2003 | Altshuler et al. |
| 2003/0095266 A1 | 5/2003 | Detalle et al. |
| 2003/0122550 A1 | 7/2003 | Kanamaru et al. |
| 2003/0129423 A1 | 7/2003 | Mastromatteo et al. |
| 2003/0189959 A1 | 10/2003 | Erbert et al. |
| 2003/0205561 A1 | 11/2003 | Iso |
| 2004/0022695 A1 | 2/2004 | Simon et al. |
| 2004/0134894 A1 | 7/2004 | Gu et al. |
| 2004/0134896 A1 | 7/2004 | Gu et al. |
| 2004/0226922 A1 | 11/2004 | Flanagan |
| 2004/0226925 A1 | 11/2004 | Gu et al. |
| 2004/0231682 A1 | 11/2004 | Stoltz et al. |
| 2004/0263950 A1 | 12/2004 | Fermann et al. |
| 2005/0035097 A1 | 2/2005 | Stoltz |
| 2005/0061779 A1 | 3/2005 | Blumenfeld et al. |
| 2005/0065502 A1 | 3/2005 | Stoltz |
| 2005/0074974 A1 | 4/2005 | Stoltz |
| 2005/0077275 A1 | 4/2005 | Stoltz |
| 2005/0107773 A1 | 5/2005 | Bergt et al. |
| 2005/0127049 A1 | 6/2005 | Woeste et al. |
| 2005/0154380 A1 | 7/2005 | DeBenedictis et al. |
| 2005/0167405 A1 | 8/2005 | Stoltz et al. |
| 2005/0171516 A1 | 8/2005 | Stoltz et al. |
| 2005/0171518 A1 | 8/2005 | Stoltz et al. |
| 2005/0177143 A1 | 8/2005 | Bullington et al. |
| 2005/0195726 A1 | 9/2005 | Bullington et al. |
| 2005/0218122 A1 | 10/2005 | Yamamoto et al. |
| 2005/0226287 A1 | 10/2005 | Shah et al. |
| 2005/0265407 A1 | 12/2005 | Braun et al. |
| 2005/0274702 A1 | 12/2005 | Deshi |
| 2006/0064079 A1 | 3/2006 | Stoltz et al. |
| 2006/0081101 A1 | 4/2006 | Hayashi et al. |
| 2006/0084957 A1 | 4/2006 | Delfyett et al. |
| 2006/0096426 A1 | 5/2006 | Park |
| 2006/0096962 A1 | 5/2006 | Park |
| 2006/0131288 A1 | 6/2006 | Sun et al. |
| 2006/0159137 A1 | 7/2006 | Shah |
| 2006/0249816 A1 | 11/2006 | Li et al. |
| 2007/0151961 A1 | 7/2007 | Kleine et al. |
| 2007/0166965 A1 | 7/2007 | Tanaka et al. |
| 2007/0215581 A1 | 9/2007 | Kato et al. |
| 2008/0050078 A1 | 2/2008 | Digonnet et al. |
| 2008/0058781 A1 | 3/2008 | Langeweyde et al. |
| 2009/0020511 A1 | 1/2009 | Kommera et al. |
| 2009/0045176 A1 | 2/2009 | Wawers et al. |
| 2009/0290151 A1 | 11/2009 | Agrawal et al. |
| 2010/0013036 A1 | 1/2010 | Carey |
| 2010/0072183 A1 | 3/2010 | Park |
| 2010/0181284 A1 | 7/2010 | Lee et al. |
| 2010/0276405 A1 | 11/2010 | Cho et al. |
| 2011/0049765 A1 | 3/2011 | Li et al. |
| 2011/0287607 A1 | 11/2011 | Osako et al. |
| 2012/0152915 A1 | 6/2012 | Srinivas et al. |

FOREIGN PATENT DOCUMENTS

| | | |
|---|---|---|
| EP | 0691563 | 1/1996 |
| EP | 1462831 | 9/2004 |
| GB | 2331038 A | 12/1999 |
| JP | 405104276 A | 4/1993 |
| JP | 8171103 | 7/1996 |
| JP | 11189472 | 7/1999 |
| JP | 2003181661 | 7/2003 |
| JP | 2003344883 | 12/2003 |
| JP | 2005174993 | 6/2005 |
| WO | WO9428972 | 12/1994 |
| WO | WO2004105100 | 12/2004 |
| WO | WO2004114473 | 12/2004 |
| WO | WO2005018060 | 2/2005 |
| WO | WO2005018061 | 2/2005 |
| WO | WO2005018062 | 2/2005 |
| WO | WO2005018063 | 2/2005 |
| WO | WO2007034317 | 3/2007 |

OTHER PUBLICATIONS

Anastassiou et al., "Photonic Bandgap Fibers Exploiting Omnidirectional Reflectivity Enable Flexible Delivery of Infrared Lasers for Tissue Cutting," Proceedings of the SPIE—the International Society for Optical Engineering, SPIE, US, vol. 5317, No. 1, Jan. 1, 2004, pp. 29-38, XP002425586 ISSN: 0277-786X.

Benoit, G. et al., "Dynamic All-optical Tuning of Transverse Resonant Cavity Modes in Photonic Bandgap Fibers, "Optics Letters, vol. 30, No. 13, Jul. 1, 2005, pp. 1620-1622.

Chen, L. et al., "Ultrashort Optical Pulse Interaction with Fibre Gratings and Device Applications," 1997, Canaga, located at http://www.collectionscanada.ca/obj/s4/f2/dsk2/ftp04/mq29402.pfd.

Chen, X. et al., "Highly Birefringent Hollow-core Photonic Bandgap Fiber," Optics Express, vol. 12, No. 16, Aug. 9, 2004, pp. 3888-3893.

Chen, Y. et al., "Dispersion-Managed Mode Locking", Journal of the Optical Society of America B, Nov. 1999, pp. 1999-2004, vol. 16, No. 11, Optical Society of America.

Dasgupta, S. et al., "Design of Dispersion-Compensating Bragg Fiber with an Ultrahigh Figure of Merit," Optics Letters, Aug. 1, 2005, vol. 30, No. 15, Optical Society of America.

De Matos et al., "Multi-kilowatt, Picosecond Pulses from an All-fiber Chirped Pulse Amplification System Using Air-core Photonic Bandgalp Fiber", Lasers and Electro-optics, 2004, (CLEO), Conference on San Francisco, CA USA, May 20-21, 2004, Piscataway, NJ, USA, IEEE, vol. May 17, 2004, pp. 973-974, XP010745448 ISBN: 978-1-55752-777-6.

De Matos, C.J.S. et al., "All-fiber Chirped Pulse Amplification using Highly-dispersive Air-core Photonic Bandgap Fiber," Nov. 3, 2003, Optics Express, pp. 2832-2837, vol. 11, No. 22.

Delfyett, P. et al., "Ultrafast Semiconductor Laser-Diode-Seeded Cr:LiSAF Rengerative Amplifier System", Applied Optics, May 20, 1997, pp. 3375-3380, vol. 36, No. 15, Octoical Society of America.

Eggleton, et al., "Electrically Tunable Power Efficient Dispersion Compensating Fiber Bragg Grating," IEEE Photonics Technology Letters, vol. 11, No. 7, pp. 854-856, Jul. 1999.

Engeness et al., "Dispersion Tailoring and Compensation by Modal Interations in Omniguide Fibers," Optics Express, May 19, 2003, pp. 1175-1196, vol. 11, No. 10.

Fink et al., "Guiding Optical Light in Air Using an All-Dielectric Structure," Journal of Lightwave Technology, Nov. 1999, pp. 2039-2041, vol. 17, No. 11.

Folkenberg, J.R., et al., "Broadband Single-polarization Photonic Crystal Fiber," Optics Letters, vol. 30, No. 12, Jun. 15, 2005, pp. 1446-1448.

Folkenberg, J.R., et al., "Polarization Maintaining Large Mode Area Photonic Crystal Fiber," Optics Express vol. 12, No. 5, Mar. 8, 2004, pp. 956-960.

Futami, F., et al., "Wideband Fibre Dispersion Equalisation up to Fourth-order for Long-distance Sub-picosecond Optical Pulse Transmission," Electronics Letters, vol. 35, No. 25, Dec. 9, 1999.

Galvanauskas, A. et al., "Chirped-pulse-amplification Circuits for Fiber Amplifiers, Based on Chirped-period Quasi-phase, matching gratings", Optics Letters, Nov. 1, 1998, p. 1695-1697, vol. 23, No. 21, Optical Society of America.

Hartl et al., "In-line high energy Yb Fiber Laser Based Chirped Pulse Amplifier System", Laser and Electro-Optics, 2004, (CLEO) Conference of San Francisco, CA USA May 20-21, 2004, Piscataway, NJ, USA, IEEE, vol. 1, May 17, 2004, pp. 563-565, XP010745382, ISBN: 978-1-55752-777-6.

Hellstrom, E. et al., "Third-order Dispersion Compensation Using a Phase Modulator", Journal of Lightwave Technology, vol. 21, No. 5, pp. 1188-1197, May 2003.

Heritage, J. P. et al., "Picosecond Pulse Shaping by Spectral Phase and Amplitude Manipulation," Optics Letters, vol. 10, No. 12, pp. 609-611, Dec. 1985.

(56) References Cited

OTHER PUBLICATIONS

Heritage, J.P. et al., "Spectral Windowing of Frequency-Modulated Optical Pulses in a Grating Compressor," Applied Physics Letters, vol. 47, No. 2, pp. 87-89, Jul. 15, 1985.

Hill, K. et al., "Fiber Bragg Grating Technology Fundamentals and Overview," Journal of Lightwave Technology, Aug. 1997, vol. 15, No. 8, pp. 1263-1276.

Ibanescu et al., "Analysis of Mode Structure in Hollow Dielctric Waveguide Fibers, "Physical Review E 67, 2003, The American Physical Society.

Jiang, et al., "Fully Dispersion Compensated ~500 fs Pulse Transmission Over 50 km Single Mode Fiber," Optics Letters, vol. 30, No. 12, pp. 1449-1451, Jun. 15, 2005.

Jiang, et al., "Fully Dispersion Compensated ~500 fs Pulse Transmission Over 50 km Single Mode Fiber," Purdue University ECE Annual Research Summary, Jul. 1, 2004-Jun. 30, 2005.

Killey, et al., "Electronic Dispersion Compensation by Signal Predistortion Using Digital Processing and a Dual-Drive Mach-Zehnder Modulator," IEEE Photonics Technology Letters, vol. 17, No. 3, pp. 714-716, Mar. 2005.

Kim, K. et al., "1.4kW High Peak Power Generation from an All Semiconductor Mode-locked Master Oscillator Power Amplifier System Based on eXtreme Chirped Pulse Amplification (X-CPA)", Optics Express, Jun. 2, 2005, pp. 4600-4606, vol. 13, No. 12.

Koechner, "Solid State Laser Engineering", Oct. 29, 1999, Section 5.5, pp. 270-277, 5th Edition, Springer.

Kwon, et al., "Tunable Dispersion Slope Compensator Using a Chirped Fiber Bragg Grating Tuned by a Fan-shaped Thin Metallic Heat Channel," IEEE Photonics Technology Letters, vol. 18, No. 1, pp. 118-120, Jan. 1, 2006.

Kyungbum, Kim et al., "1.4kW High Peak Power Generation from an all Semiconductor Mode-locked Master Oscillator Power Amplifier System Based on eXtreme Chirped Pulse Amplification (X-CPA)", Optics Express, Jun. 2, 2005, pp. 4600-4606, vol. 13, No. 12.

Levy et al., "Engineering Space-Variant Inhomogeneous Media for Polarization Control," Optics Letters, Aug. 1, 2004, pp. 1718-1720, vol. 29, No. 15, Optical Society of America.

Liao, Kai-Hsiu et al., "Large-aperture Chirped Volume Bragg Grating Based Fiber CPA System,"Optics Express, Apr. 16, 2007, Volume15, No. 8, pp. 4876-4882.

Limpert et al., "All Fiber Chiped-Pulse Amplification System Based on Compression in Air-Guiding Photonic Bandgap Fiber", Optics Express, Dec. 1, 2003, vol. 11, No. 24, pp. 3332-3337.

Lo, S. et al., "Semiconductor Hollow Optical Waveguides Formed by Omni-directional Reflectors", Optics Express, vol. 12, No. 26, Dec. 27, 2004, pp. 6589-6593.

Malinowski A. et al., "Short Pulse High Power Fiber Laser Systems," Proceedings of the 2005 Conference on Lasers and Electro-Optics (CLEO), Paper No. CThG3, pp. 1647-1649, May 26, 2005.

Mehier-Humbert, S. et al., "Physical Methods for Gene Transfer: Improving the Kinetics of Gene Delivery Into Cells," Advanced Drug Delivery Reviews, vol. 57, pp. 733-753, 2005.

Mohammed, W. et al., "Selective Excitation of the TE01 Mode in Hollow-Glass Waveguide Using a Subwavelength Grating," IEEE Photonics Technology Letters, Jul. 2005, vol. 17, No. 7, IEEE.

Nibbering, E.T.J., et al. "Spectral Determination of the Amplitude and the Phase of Intense Ultrashort Optical Pulses," Journal Optical Society of America B, vol. 13, No. 2, pp. 317-329, Feb. 1996.

Nicholson, J. et al., "Propagation of Femotsecond Pulses in Large-mode-area, Higher-order-mode Fiber," Optics Letters, vol. 31, No. 21, 2005, pp. 3191-3193.

Nishimura et al., "In Vivo Manipulation of Biological Systems with Femtosecond Laser Pulses," Proc. SPIE 6261, 62611J, pp. 1-10, 2006.

Noda, J. et al., "Polarization-maintaining Fibers and Their Applications", Journal of Lightwave Technology, vol. Lt-4, No. 8 Aug. 1986, pp. 1071-1089.

Palfrey et al., "Generation of 16-FSEC Frequency-tunable Pulses by Optical Pulse compression" Optics Letters, OSA, Optical Society of america, Washington, DC, USA, vol. 10, No. 11, Nov. 1, 1985, pp. 562-564, XP000710358 ISSN: 0146-9592.

Pelusi, M. et al. "Electrooptic Phase Modulation of Stretched 250-fs Pulses for Suppression of Third-Order Fiber Disperson in Transmission", IEEE Photonics Technology Letters, vol. 11, No. 11, Nov. 1999, pp. 1461-1463.

Pelusi, M. D. et al., "Phase Modulation of Stretched Optical Pulses for Suppression of Third-order Dispersion Effects in fibre Transmission," Electronics Letters, vol. 34, No. 17, pp. 1675-1677, Aug. 20, 1998.

Price et al., "Advances in High Power, Short Pulse, Fiber Laser Systems and Technology", Photonics West 2005, San Jose, California, Jan. 2005, pp. 5709-3720.

Price et al., "Advances in High Power, Short Pulse, Fiber Laser Systems and Technology", Proceedings of SPIE—vol. 5709, Fiber Lasers II: Technology, Systems, and Applications, Apr. 2005, pp. 184-192.

Ramachandran, S., et al., "High-power Amplification in a 2040-$\mu m^2$ Higher Order Mode," SPIE Photonics West 2007, Post-deadline.

Resan et al., "Dispersion-Managed Semiconductor Mode-Locked Ring Laser", Optics Letters, Aug. 1, 2003, pp. 1371-1373, vol. 28, No. 15, Optical Society of America.

Schreiber, T., et al., "Design and High Power Operation of a Stress-induced single Polarization Single-transverse Mode LMA Yb-doped Photonic Crystal Fiber," Fiber Lasers III: Technology, Systems, and Applications, Andrew J.W. Brown, Johan Nilsson, Donald J. Harter, Andreas Tünnermann, eds., Proc. of SPIE, vol. 6102, pp. 61020C-1-61020C-9, 2006.

Schreiber, T., et al., "Stress-induced Single-polarization Single-transverse Mode Photonic Crystal Fiber with Low Nonlinearity," Optics Express, vol. 13, No. 19, Sep. 19, 2005, pp. 7621-7630.

Siegman, "Unstable Optical Resonators", Applied Optics, Feb. 1974, pp. 353-367, vol. 13, No. 2.

Stevenson et al., Femtosecond Optical Transfection of Cells: Viability and Efficiency, Optics Express, vol. 14, No. 16, pp. 7125-7133, Aug. 7, 2006.

Stock et al., "Chirped Pulse Amplification in an Erbium-doped fiber Oscillator/Erbium-doped Fiber Amplifier System", Optics Communications, North-Holland Publishing Co., Amsterdam, NL, vol. 106, No. 4/5/06, Mar. 15, 1994, pp. 249-252, XP000429901, ISSN: 0030-4018.

Strickland et al., "Compression of Amplified Chirped Optical Pulses", Optics Communications, North-Holland Publishing Co., Amersterdam, NL, vol. 56, No. 3, Dec. 1, 1985, pp. 219-221, XP024444933 ISSN: 0030-4018 (retrieved on 1985-12-011.

Temelkuran, B. et al., "Wavelength-scalable Hollow Optical Fibres with Large Photonic Bandgaps for CO2 Laser Transmission," Nature, Dec. 12, 2002, pp. 650-653.

Thurston, R.N. et al., "Analysis of Picosecond Pulse Shape Synthesis by Spectral Masking in a Grating Pulse Compressor," IEEE Journal of Quantum Electronics, vol. EQ-22, No. 5, pp. 682-696, May 1986.

Tirlapur et al., "Targeted Transfection by Femtosecond Laser," Nature Publishing Group, vol. 418, pp. 290-291, Jul. 18, 2002.

Tsai et al., "Ultrashort Pulsed Laser Light," Optics & Photonics News, pp. 25-29, Jul. 2004.

Vaissie et al., "Desktop Ultra-Short Pulse Laser at 1552 nm,"Ultrashort Pulse Laser Materials Interaction Workshop (Raydiance)—Directed Energy Professional Society (DEPS), Sep. 28, 2006.

Weiner, A.M. et al., "Synthesis of Phase-coherent, Picosecond Optical Square Pulses," Optics Letters, vol. 11, No. 3, pp. 153-155, Mar. 1986.

Weiner, A.M., "Femtosecond Optical Pulse Shaping and Processing," Prog. Quant. Electr. 1995, vol. 19, pp. 161-237, 1995.

Weiner, A.M., "High-resolution femtosecond Pulse Shaping," Journal of the Optical Society of America B. vol. 5, No. 8, pp. 1563-1572, Aug. 1988.

Wells, D.J., "Gene Therapy Progress and Prospects: electroporation and Other Physical Methods," Gene Therapy, Nature Publishing Group, vol. 11, pp. 1363-1369, Aug. 5, 2004, (http://www.nature.com/gt).

(56) References Cited

OTHER PUBLICATIONS

White, W.E., et al., "Compensation of Higher-order Frequency-dependent Phase Terms in Chirped-pulse Amplification Systems," Optics Letters, vol. 18, No. 16, pp. 1343-1345, Aug. 15, 1993.

Yamakawa et al., "1 Hz, 1 ps, terawatt Nd: glass laser", Optics Communications, North-Holland Publishing Co. Amsterdam, NL, vol. 112, No. 1-2, Nov. 1, 1994, pp. 37-42, XP024424285.

Yan et al., Ultrashort Pulse Measurement Using Interferometric Autocorrelator Based on Two-photon-absorbtion Detector at 1.55µm Wavelength Region., 2005, Proceedings of SPIE vol. 5633, Advanced Materials and Devices for Sensing and Imaging II, pp. 424-429.

Yeh, et al. "Theory of Bragg Fiber", Journal of the Optical Society America, Sep. 1978, pp. 1196, vol. 68, No. 9., pp. 1196-1201.

Yi, Y. et al., "Sharp Bending of On-Chip silicon Bragg Cladding Waveguide With Light Guiding on Low Index Core Materials", IEEE Journal of Selected Topics in Quantum Electronics, vol. 12, No. 6, Nov./Dec. 2006, pp. 1345-1348.

Yi, Y., et al., "On-chip Si-based Bragg Cladding Waveguide with High Index Contrast Bilayers", Optics Express, vol. 12, No. 20, Oct. 4, 2004, pp. 4775-4780.

Yin, D. et al., "Integrated ARROW Waveguides with Hollow Cores", Optics Express, vol. 12, No. 12, Jun. 14, 2004, pp. 2710-2715.

Zhou, S. et al., "Compensation of nonlinear Phase Shifts with Third-order Dispersion in Short-pulse Fiber Amplifiers," Optics Express, vol. 13, No. 13, pp. 4869-2877, Jun. 27, 2005.

\* cited by examiner

US 8,884,184 B2

POLYMER TUBING LASER MICROMACHINING

CROSS-REFERENCES TO RELATED APPLICATIONS

This application claims the priority benefit of U.S. provisional patent application No. 61/373,201, filed Aug. 12, 2010, and titled "Polymer Tubing Laser Micromachining and Holding Mechanism." The disclosure of the aforementioned application is incorporated herein by reference in its entirety.

BACKGROUND

A stent is an artificial "tube" or cylindrical device inserted into a natural passage in the body to prevent a localized flow constriction. For example, a coronary stent is a cylindrical device placed in a coronary artery that supply the heart in order to keep the arteries open in the treatment of coronary heart disease. Traditionally, coronary stents consisted of a metal framework that could be placed inside the artery to help keep it open. However, as the stent is a foreign object, it incites an immune response. This may cause scar tissue to rapidly grow over the stent. In addition, there is a strong tendency for clots to form at the site where the stent comes into apposition with the arterial wall. To address these issues, a new generation of stent has been developed with biodegradable polymers.

A polymer stent can be manufactured using the process of laser ablation of a polymer tube, a process in which a laser device irradiates the polymer tube with a laser beam. The irradiation helps to remove closed contoured sections from the polymer tube, thereby creating a polymer framework of the stent.

However, a number of issues can occur when cutting a specific pattern in a polymer tube. For example, the polymer tube may not exactly follow the pattern programmed in the laser device because of the torsion occurring as the polymer tube is moved around by a holding mechanism. Another issue may relate to the polymer tube bending as the high-pressure process gas is used to remove debris during the athermal ablation. Yet another issue may relate to the polymer sections bending as they are being cut away.

The fabrication of cardiovascular stents or other medical devices designed for implantation in the human body require extreme precision in feature size and location and the current generation of tube cutting workstations are inadequate to achieve the necessary fidelity to a computer generated design when machining novel materials (e.g. polymers).

SUMMARY

Provided is an apparatus for the athermal ablation of a workpiece. In some example embodiments, the apparatus includes a laser device to direct a laser beam at the workpiece to remove a plurality of sections from the workpiece using athermal ablation, with the removal occurring in a plurality of discrete motions that cause the laser beam to trace along outer perimeters of the plurality of sections in a specific order so as to maintain mechanical stability of the plurality of sections. The apparatus may further include a process gas nozzle to deliver process gas substantially coaxially with the laser beam, with the process gas clearing debris resulting from the laser ablation of the workpiece. The apparatus may further include a workpiece holder to hold, and maneuver the workpiece during the removal of the plurality of sections. The apparatus may further include a workpiece support to support and stabilize the workpiece during the removal of the plurality of sections.

The workpiece may include one or more polymer materials. The workpiece holder may include a mandrel to support the workpiece from the inside during the ablation process. The mandrel may include at least an outer layer composed of the same material as the workpiece. The mandrel may be pressurized with a gas to increase and decrease the size of the mandrel so as to grip and release the workpiece. The mandrel may include a spring-loaded mechanism to grip and release the workpiece. The mandrel may include an inner core that is tapered for ease of insertion and extraction. The mandrel's inner core may include a metal or a glass. The workpiece may be substantially flat or tubular.

The laser beam may include an ultrafast laser. Parameters of the laser beam may be dynamically adjustable. The laser device may maneuver the laser beam in operation. The plurality of sections to be removed may be selected in such a way that the workpiece is moved around its axis substantially in one direction as to avoid torsional distortion.

The workpiece may be one or more of the following medical devices: an intravascular stent, a tumor encapsulator, and a catheter. However, the workpiece is not limited to being one of these devices, and may be any suitable device. The plurality of sections may be removed using a multi-pass cutting technique, with the workpiece being repetitively moved below the laser beam so that the laser beam traces outer perimeters of the plurality of sections for a plurality of passes, with each pass cutting a partial thickness of the workpiece being machined away by the laser beam until a sufficient number of passes results in the laser beam cutting through the workpiece.

The process gas nozzle may be of a tapered conical shape with a small orifice positioned above a focal point of the laser beam, with a clearance notch being cut into a side of the process gas nozzle to permit closer proximity of the workpiece support to the focal point and to improve positioning stability of the workpiece. The laser beam may cut a part of a section by starting in a first location internal to the section, then move onto the outer perimeter of the section and cut along the outer perimeter of the section, and finally move to a second location internal to the section. The section may be removed by skipping parts of the outer perimeter of the section so as to maintain mechanical stability of the section. The laser beam may achieve athermal material removal by ionization and Coulomb explosion.

These and other embodiments are described further below with reference to the figures.

DETAILED DESCRIPTION OF THE INVENTION

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

Laser micromachining is becoming prevalent in the fabrication of small precision tubular components such as intravascular stents. Traditionally, these parts have been machined from metallic materials such as nitinol or similar high strength alloys, but newer designs are being fabricated from biodegradable polymers. These polymers present new challenges for achieving the desired dimensional precision in the finished part.

Figure 1:
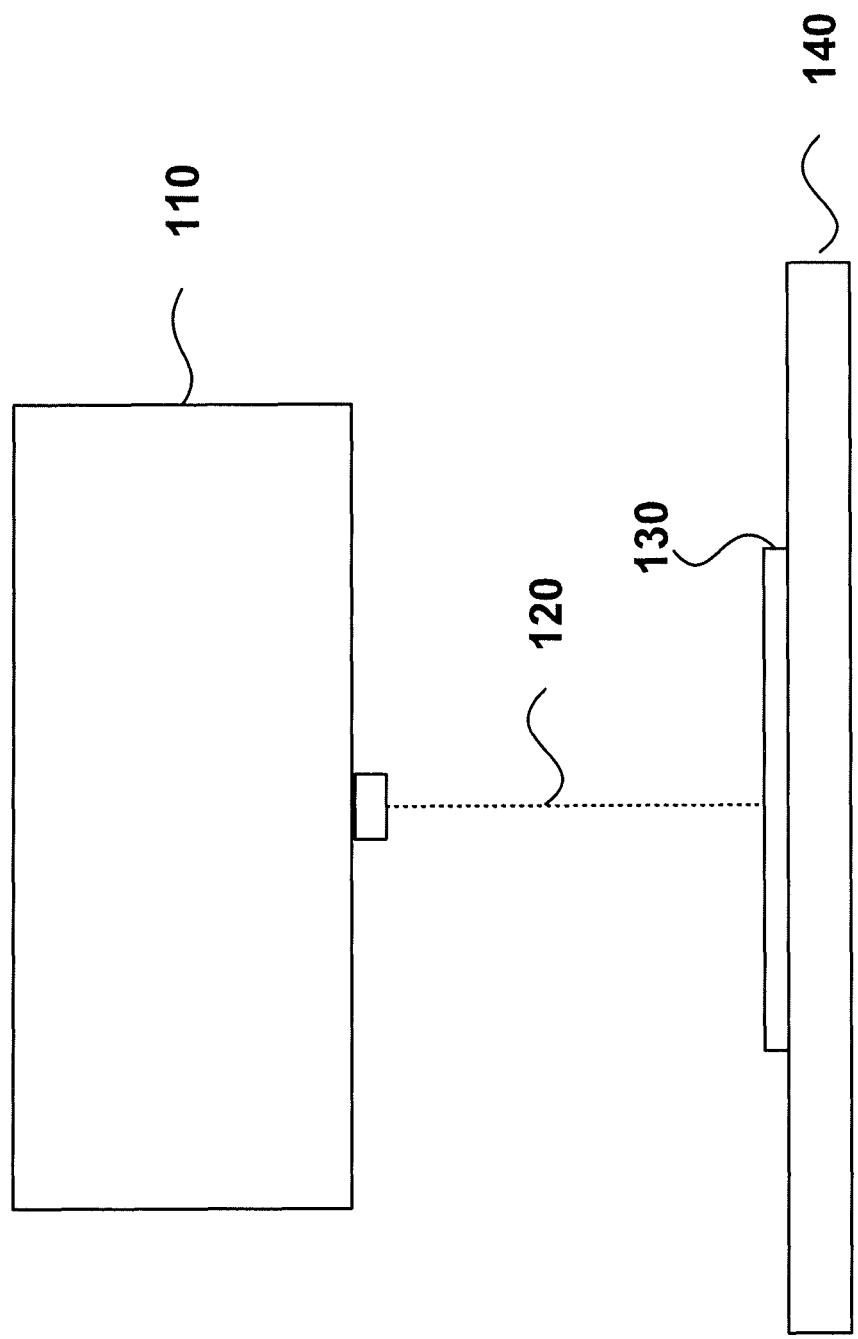
FIG. 1 is a block diagram of an exemplary laser system.

FIG. 1 is a block diagram of an exemplary ultrafast laser. FIG. 1 includes a laser device 110, a target 130, and a platform 140. Laser device 110 may direct pulses of ultrafast laser light 120 at target 130. In some embodiments, parameters of the laser may be adjusted as the laser light is directed at target 130.

The target 130 may be made of a polymer material. As shown, target 130 is substantially flat, and a polymer stent can be completed by machining target 130 first and then wrapping target 130 into a tube to complete the stent. However, it will be understood that target 130 may be of any other shape as well. For example, target 130 may be tubular in shape and be held and maneuvered by a holding device (not shown).

A polymeric stent produced by machining target 130 may be used as a medical device, including in tumor treatment (where instead of using the polymeric stent to expend an artery, it would be used to encapsulate a tumor) or as a catheter.

Figure 2:
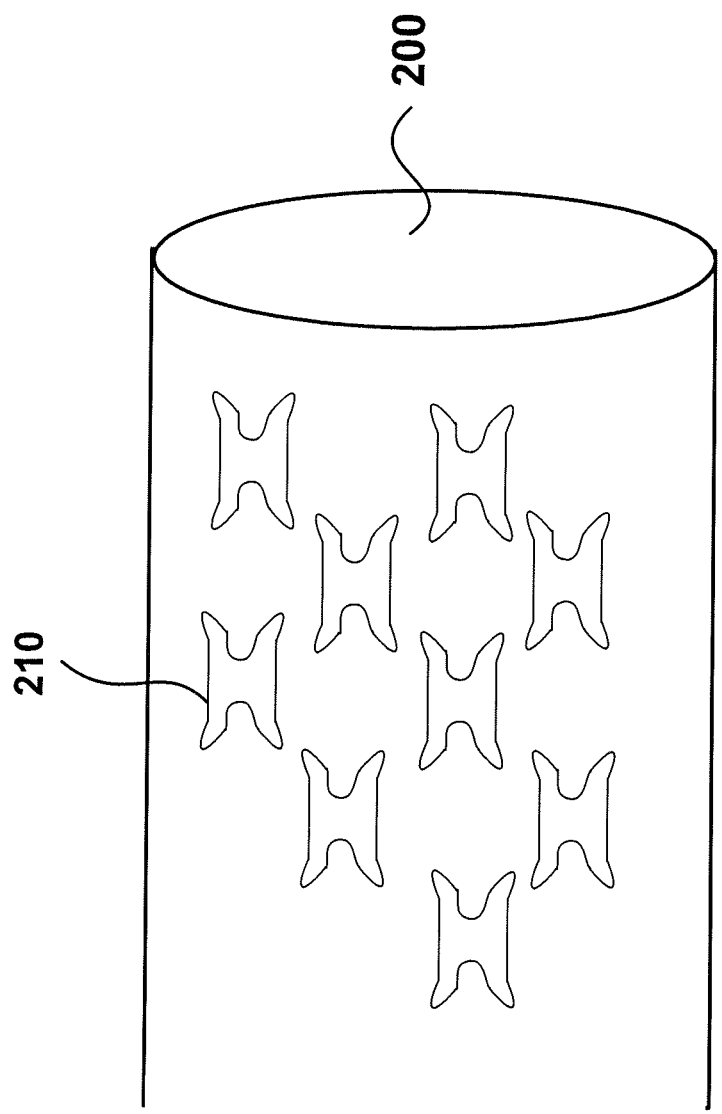
FIG. 2 illustrates a portion of an exemplary stent.

FIG. 2 illustrates an exemplary stent 200. Stents are commonly machined from a uniform hollow cylinder (a tube) having the desired outer and inner diameters. A pattern can be 'unwrapped' from a cylinder. A plurality of sections 210 represent what needs to be removed from a cylindrical workpiece to create stent 200. It is noteworthy that sections 210 can come in various shapes, depending on the design of the particular stent. These voids are left in the polymeric tube when the stent is finalized. As shown, the plurality of sections 210 are of a curved shape but other shapes and patterns can be utilized as well. In some example embodiments, straight shapes along the length of the tube can connect sections 210.

Figure 3:
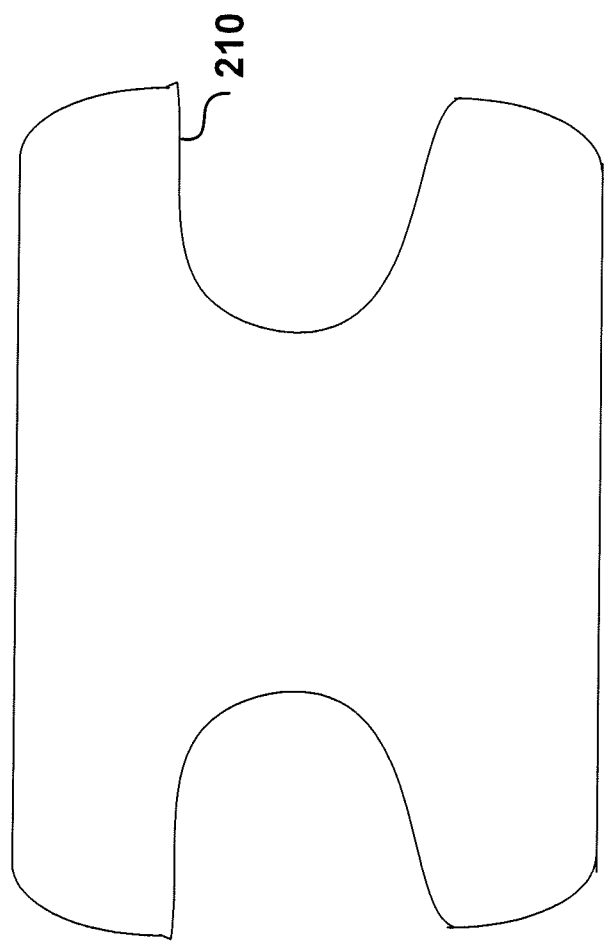
FIG. 3 illustrates an exemplary section of a stent pattern.

FIG. 3 illustrates the exemplary section 210, this time with differently shaped sections 210. The use of any other suitable shapes in contemplated. In order to create a stent pattern, the inner area of the section 210, and that of all the other sections of the pattern, is "cut out" from the starting cylindrical workpiece. This is typically accomplished by moving the cylindrical workpiece below a fixed laser beam through a series of motions that cause the laser beam to trace along the outer perimeter of the sections that need to be cut out to create the desired overall pattern.

When cutting stents from traditional metal tubes, the laser machining process is typically accomplished in a single pass of the beam along the perimeters of the sections in the pattern. Process parameters are chosen so that the laser can cut through the full thickness of the tubing wall with one pass of the laser. When cutting polymer tubing, it is often not possible to establish process conditions that allow this 'single-pass' cutting method, because the polymer material cannot dissipate heat quickly enough. As a result, progressively more aggressive process conditions lead to melting, and/or other underlying structural changes, of the polymer material before single-pass, full-wall-thickness cutting is established. A multi-pass cutting protocol may therefore be employed on polymer tubing, whereby the cylindrical workpiece is repetitively moved below the fixed laser beam so that the laser beam traces the desired cutting path several times. In this way, a partial thickness of the tubing wall is machined away by the laser with each repetition of the pattern, until a sufficient number of passes results in the laser machining through the full wall thickness.

As section 210 of the pattern is machined away, the remaining workpiece may become mechanically weaker because the integrity of the cylindrical tubing is compromised, and only thin sections of the tubing wall are left intact to support the overall structure. However the accuracy of the machining process relies on precise and repeatable positioning of the workpiece below the laser beam. This is especially true when the machining protocol requires multiple passes of the laser beam over the cutout pattern. If, as the machining pattern proceeds, loss of mechanical integrity in the workpiece result in sagging, warping, or other positional errors at the point of the machining process, the laser will not trace (or retrace) its path correctly, and the desired cutout pattern will not be accurately replicated on the workpiece. A stent may have distortions of the machined features that result from positioning errors between the workpiece and the focused laser beam during the machining process.

In some examples, two sections may theoretically have the same dimension, but positioning errors during the machining process may result in a substantial error in the as-machined dimensions of these two features. Other pattern distortions may arise from multiple causes, including errors in the accuracy of the motion control hardware of the stent cutting workstation, or errors in azimuthal orientation of the tubing at the laser cutting plane due to low torsional stiffness of the tubing, deflection of the workpiece by the process gas, sagging or displacement of the workpiece due to loss of strength/stability caused by material removal.

The workpiece is typically chucked (held) by a rotary/axial positioning system at a location remote from the actual laser machining site. Typically, the workpiece is also supported by a secondary holder (the "workpiece support") positioned in closer proximity to the laser machining site. This is typically a low friction bushing having an inner diameter that is just large enough to accommodate the workpiece tubing without binding; alternately, it may be a spring-loaded clamp with nylon or Teflon inserts having a "v"-groove that holds the axis of the workpiece in a fixed location while allowing the workpiece to rotate about its axis and translate along its axis. Motions of the tube are accomplished by moving the chuck and relying on perfect transference of those motions to the section of the workpiece that is being machined. If there is low torsional stiffness, binding at the secondary holder, or uncontrolled sagging/deflection/displacement, an angular rotation of the chuck by a specific magnitude may not move the distant end of the tube (where the laser is machining it) by the same magnitude.

Process gas is commonly delivered coaxially with the focused laser beam in a laser micromachining process. Process gas clears debris from the machining area. In some embodiments, the process gas may also serve to cool the workpiece. When the workpiece is flexible, process gas may cause deflection or displacement of the workpiece at the critical point of laser focus where machining is taking place. The process gas nozzle itself is typically a tapered conical shape that is cold formed from copper, with a small orifice positioned just a few hundred microns above the laser focus. The mechanical structure of the nozzle limits the proximity with which the workpiece support may be positioned relative to the laser focal point. If the workpiece support could be positioned closer to the laser focal point, improved positioning stability of the workpiece right at the critical location of machining would be achieved as compared with a more remote location of the workpiece support.

Another problem that may lead to machining errors is the behavior of waste cuts—pieces of the workpiece that are being cut away to create the desired pattern. Waste cuts being removed from the workpiece may loosen and become partially dislodged as the cutouts are completed, causing them to become displaced in a way that blocks the laser beam, scatters it, or mechanically distorts the workpiece while machining continues.

The present technology includes a unique set of process conditions to address these multiple sources of pattern distortion in laser micro-machined cylindrical components. These may include but are not limited to: precise adjustment of the tension on a clamp-style workpiece support that is forceful enough to maintain accurate workpiece positioning, but not so forceful as to cause binding; suitable process gas pressure that is high enough to provide the benefit of debris removal without being so forceful as to displace the workpiece at the point of machining; and chucking of the workpiece at the point of closest practical proximity to the point of laser machining, while allowing adequate range of motion to permit machining of the full pattern on the workpiece. Typically this implies that the workpiece is chucked at a location approximately one machining-pattern-length removed from the chuck's end-of-travel limit; modification of the process gas nozzle to enable closer positioning of the workpiece support to the point of laser machining; and the addition of stabilizing tabs at strategic positions along the perimeter of the pattern sections that prevent waste cuts from dislodging too early during the machining process and adversely affecting the machining results. According to some embodiments, advantageously, a laser is used to partially machine through the stabilizing tab, and the particular order(s) in which these stabilizing tabs and other sections of the contour are cut relative to each other is also carefully considered to provide advantages as discussed herein.

With respect to workpiece support tension, the tension on the workpiece support is adjusted by trial and error while rotating the chuck and applying process gas. The motion of the workpiece is typically viewed using a high magnification digital microscope to image the end of the workpiece as it is positioned below the process gas nozzle and rotated under application of process gas. Tension is adjusted until no lateral displacement of the workpiece is observed under the process gas load. A small amount of additional tension may be applied as a safety margin. Tension on a workstation is not measured directly, but is based on position readings on a micrometer that adjusts spring tension on the workpiece support.

Process gas may include helium when machining polymers. Process gas pressure depends on the type of thickness polymer being machined. Process gas pressures between 5 psi and 35 psi are typically used; however any suitable pressures may be used.

The chuck may be positioned behind its end-of-travel limit by an amount equal to the length of the pattern being machined, plus a few millimeters of additional clearance to allow for tube positioning during the machining process. This minimizes the distance between the machining location and the clamping position of the workpiece. Maintaining a minimum distance between these points helps to reduce azimuthal positioning errors resulting from low torsional stiffness of the workpiece.

A clearance notch may be cut into the side of the process gas nozzle to permit closer proximity of the workpiece support to the laser focal point, thereby improving workpiece positioning stability at the critical laser machining location.

To manage the behavior of waste cuts, pattern sections can be divided into multiple short segments rather than one continuous perimeter cut. Some of the perimeter segments are very short and are positioned at strategic locations along the perimeters of the sections. The segments are machined in a specific order to control the process. To describe the newly developed machining protocol for polymers, the concept of lead-ins and lead-outs is explained with reference to FIG. 4.

Figure 4:
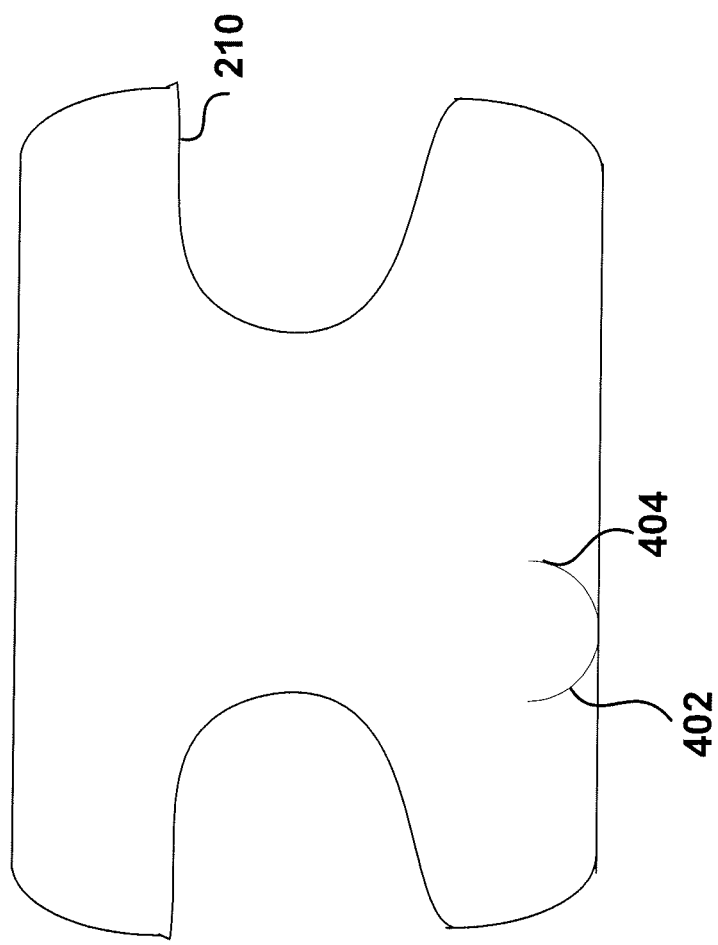
FIG. 4 illustrates a typical lead-in and lead-out of a pattern section, in accordance with an exemplary embodiment.

FIG. 4 illustrates a typical pattern section 210. In traditional laser machining, a laser device is not turned on and off directly on the contour of the section 210 to avoid an undesirable effect on contour. Therefore, to maintain dimensionality and the desired pattern, the laser device may be turned on inside the section 210 and then moved onto the contour via a lead-in 402 and then moved off it via a lead-off 404 before the laser device is turned off. When the section 210 is removed, the laser device moves onto the next section and the process is repeated.

The central area of the section 210 represents the waste cut—a section of the workpiece to be removed by the machining process. (In the drawing figures, the machining pattern has been "unwrapped" from the cylindrical shape of the workpiece and depicted flat for purposes of clarifying the illustrations and accompanying discussion.)

The border of section 210 represents the outline of the pattern section that is to be cut using the laser machining process. The short, curved lines represent the lead-in and lead-out paths respectively. As mentioned above, the laser does not begin to machine a given pattern section directly on the perimeter of the cut, but typically begins to cut each section at a location internal to the cutout, within the waste cut zone, and then quickly moves along a straight or curved line onto the cutout perimeter, where it then proceeds to cut along the perimeter of the cutout until it arrives back at the starting location. At that point, the laser is again moved along a straight or curved line back into the waste cut area. In this way, the path of the laser around the perimeter of the pattern section is akin to a car getting on and off a freeway using an on-ramp and off-ramp.

Figure 5:
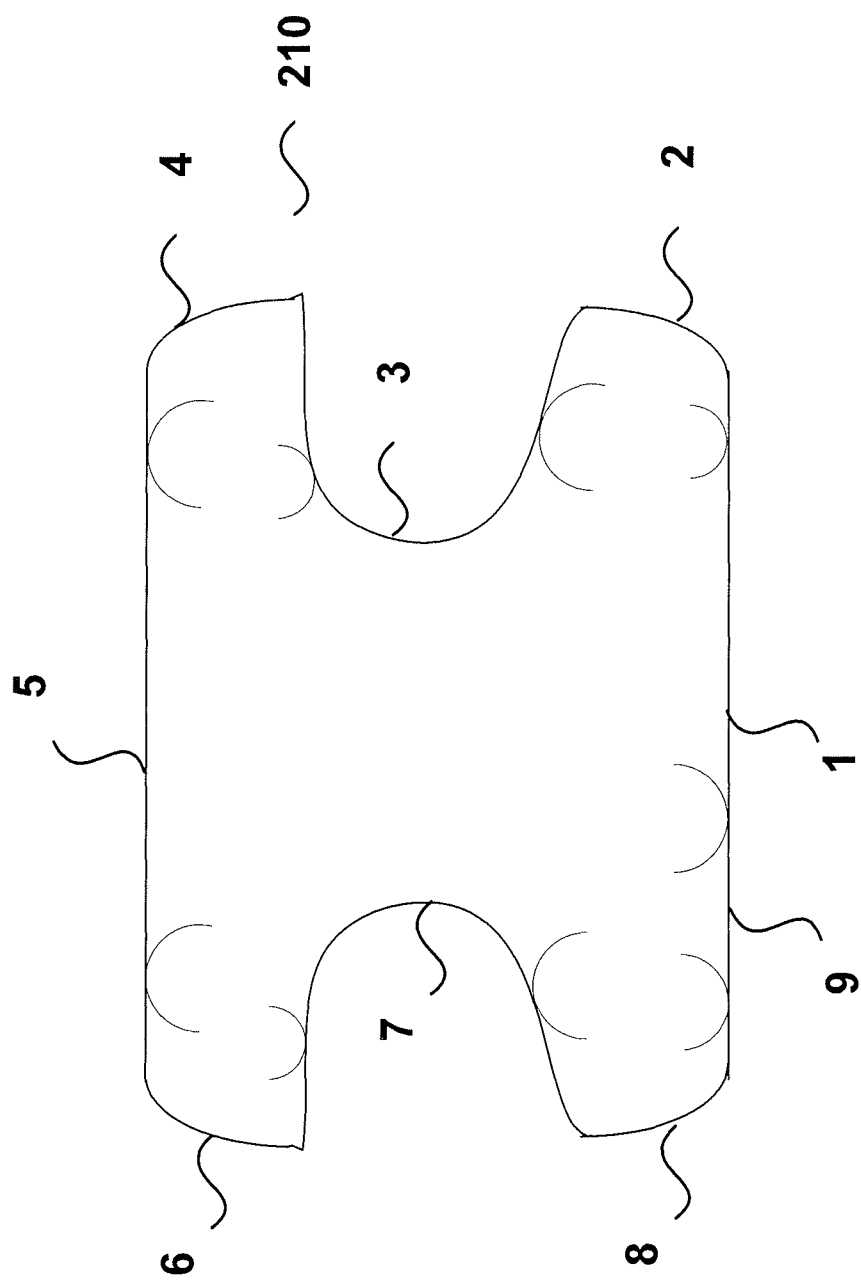
FIG. 5 illustrates multiple lead-ins and lead-outs positioned along a pattern section perimeter, in accordance with an exemplary embodiment.

Ordinarily, a pattern section such as the one shown would utilize only a single lead-in/lead-out pair as illustrated above, and the laser would trace along this path as many times as necessary to cut through the full thickness of the tubing wall. As shown in FIG. 5, in an improved machining process, multiple lead-ins and lead-outs are positioned along the perimeter of the pattern segments.

FIG. 5 illustrates multiple lead-ins and lead-outs positioned along a pattern section perimeter. The laser device can be turned on and off and cut different segments of the section 210. It may be advantageous to have some of these lead-ins and lead-outs instead of a single lead-in and one lead-out for the entire section 210 because it provides for stabilizing section 210 by maintaining the alignment of section 210 with the surrounding structure of the stent. The laser device may be moved in a specific order so that it does not cut every one of these sections for the entire contour at once.

If, on the other hand, the section 210 is cut out in a single pass, by the time the last part is cut, the entire section 210 may be misaligned with the rest of the surrounding structure, thereby losing mechanical stability, which in turn affects the precision of the laser ablation. The pattern of FIG. 5 may be broken up into multiple short segments, as noted by the segment numbers 1-9.

The multiple short segments 1-9 of a pattern section illustrated in FIG. 5, in some exemplary embodiments, can be cut in succession to a certain depth. This multi-pass technique aims to maintain structural stability and may allow cutting the same pattern, (for example, 5 or 7 times) with each pass only cutting a partial thickness through the section. FIG. 5 illustrates how segments 1-9 can be cut in a specific order, through a partial depth of the section 210. In 10 passes, all 9 segments can be cut.

In some embodiments, cuts can be ordered so that instead of intermittently moving the workpiece clockwise and counterclockwise, the workpiece can be moved in the same direction. This approach is advantageous because it eliminates torsion and twisting resulting from changing directions of the holding mechanism. When a rotary motor rotating the holding mechanism continues turning in the same direction, there are no torsional forces that might result in miscutting of the tube. If, on the other hand, the workpiece is intermittently turned clockwise and counterclockwise, torsion in the tube may result.

In some example embodiments, instead of cutting each segment of the section over in several passes, each segment is cut all the way through in a specific order. This approach results in a low variation of the section width.

The perimeter segments, along with corresponding lead-in and lead-out paths, may be thought of as separate, discontinuous entities in some embodiments. In practice, these segments may be machined in proper relation to one another in order to create the overall pattern segment.

When this pattern section is machined, in some embodiments, the laser first traces out all of the perimeter segments in order (e.g. 1 through 9 going around the section 210 counter-clockwise and beginning with the perimeter segment at the bottom of section 210.) so that the entire patterned is machined through a partial thickness of the tubing wall. This is repeated several times, until only one or two additional passes of the laser are required to break through the full tubing wall thickness. For example, if a given polymer tube requires seven (7) passes of the laser along a machined pathway in order to cut through the full tubing wall thickness, only five or six passes of the laser might be traced over the full pattern. Following this, the laser may be traced only over segments 1, 3, 5, 7, and 9, while skipping segments 2, 4, 6, and 8. The odd-numbered segments may be machined in order, one after the other, for the one or two additional repetitions that are required to break through the full wall thickness only along those segments.

Following this, the waste cut may be held in place only by the short connecting tabs at locations 2, 4, 6, and 8. These connecting tabs are thinner than the original tubing wall thickness because of the initial full-perimeter passes of the laser. Only one or two remaining passes of the laser over these connecting tabs are required to break the waste cut free from the workpiece. At this point, the connecting tabs are machined away in a sequence that minimizes any chance for the waste cut, now freed from the workpiece, to interfere with the machining process before the final cut is created. In the figures, segments 8, 6, 4, and 2 may be machined in that order. In the case that two additional passes of the laser are required to cut through the full tubing wall thickness, each of the segments may be machined through its full thickness before proceeding to the next segment in the cutoff machining sequence. For example, segment 8 may be traced by the laser two additional times, freeing the waste cut at that location before proceeding with the machining of segment 6, and so on.

The present technology may be used to position and maneuver a polymer tube for purpose of micromachining the tube using a laser beam. Whereas previous tube micromachining has been achieved while simply holding and positioning a tube within a single three-jaw, self-centering chuck—similar to a mechanical lathe set-up—the new generation of tube materials (including polymers) may be too flexible to remain rigid as parts of its sidewalls are machined away. This would be especially true when a jet of inert gas is directed at the tube simultaneous with the laser beam, where the gas jet aids the machining process by removing particulate debris from the laser beam path. There are other benefits to using "process gas" as well.

Figure 6:
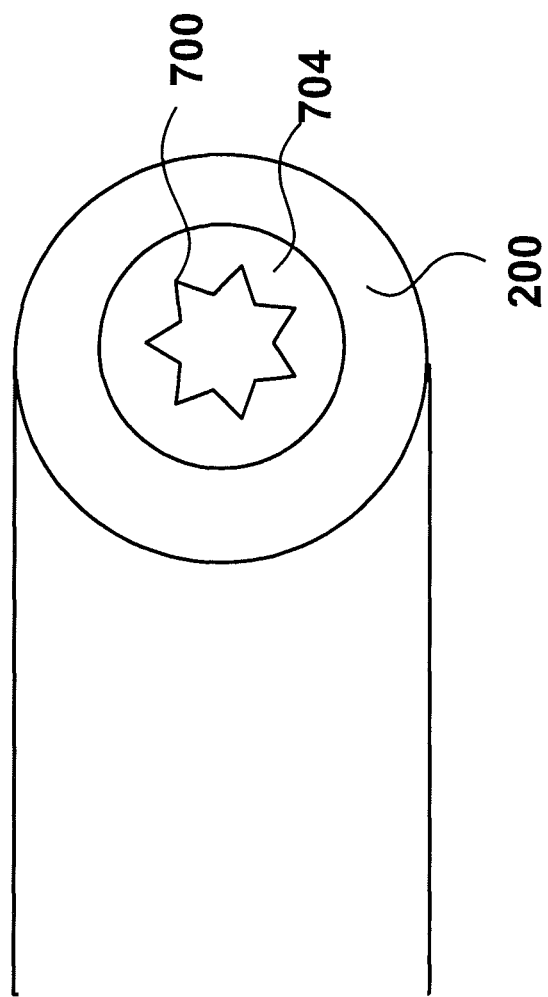
FIG. 6 illustrates a mandrel and a polymer tube, in accordance with an exemplary embodiment.

FIG. 6 illustrates a mandrel 700 for holding and maneuvering the polymer tube 200. In some example embodiments, the polymer tube 200 may be held by a chuck, and the portion of the polymer tube being machined may be suspended in free space without adequate support. In this case, process gas may be applied from above, coaxial with the laser beam. Hence, the downward pressure of the gas may slightly bend or otherwise modify the polymer tube during laser exposure. The transient bending of the tube may result in non-optimal alignment with the laser beam. Deleterious results include: incomplete machining, erroneous feature sizes, and/or laser exposure at undesirable locations or times. Any of these results may yield the finished tube-based part as unacceptable or waste.

The present technology provides means to hold and maneuver the tube with reliable rigidity and exquisite precision in position, even when strong gas pressure jets are applied to the part during machining. The concept includes use of the mandrel 700 to support the polymer tube 200 from the inside during the micromachining process. The mandrel 700 may provide sufficient rigidity that remains consistent throughout the process, since it is not intentionally machined during the process. The mandrel 700 may have at least an outer layer (not shown) composed of the material similar or identical to the polymer tube 200 being machined. This may be advantageous to reduce cross-contamination between the tube material and any nearby materials. Since the machining is performed by way of laser ablation, dissimilar materials can be transferred between tube 200 and mandrel 700 by micro-explosion and redeposit of matter.

In some embodiments according to the present technology, the mandrel is shaped in such a way as to only contact and support the tube in locations that border the perimeter cuts, on the outside of the perimeter cuts, such that the tube is supported in locations that remain after the waste cuts are removed.

In some embodiments according to the present technology, the mandrel 700 is tapered for ease of insertion and extraction, where the fully inserted mandrel 700 provides outward mechanical force on the tube to maintain substantial friction and support against the inner wall of the polymer tube 200.

Figure 7:
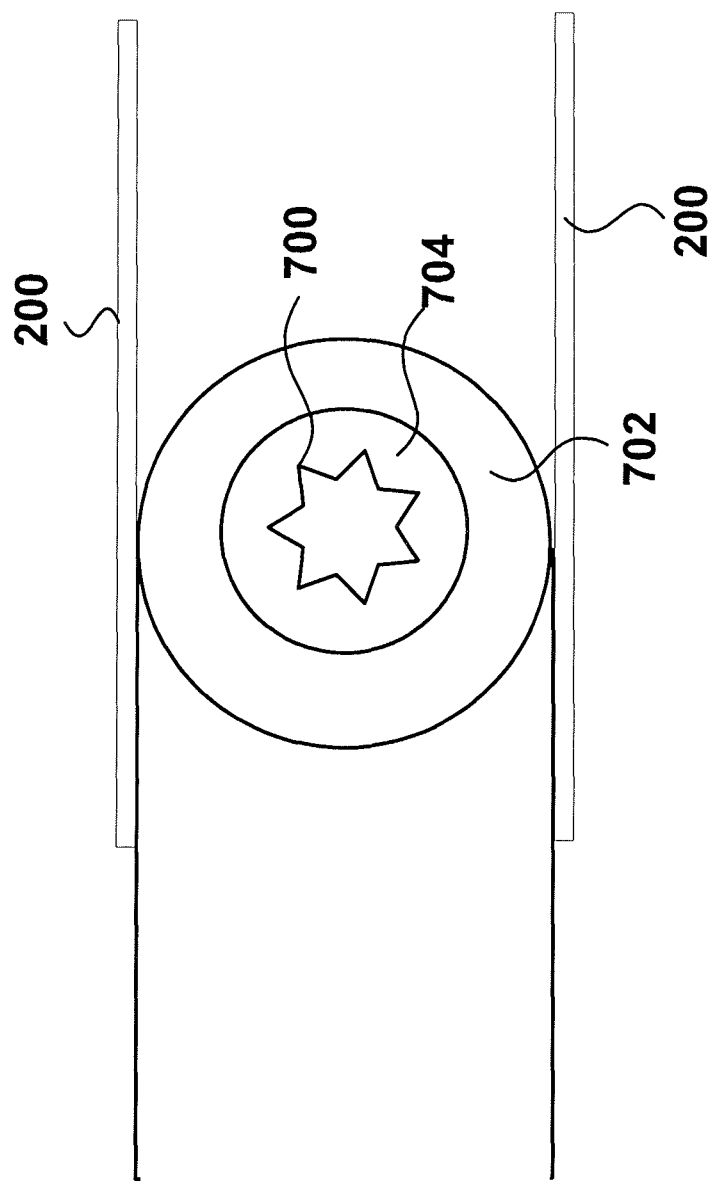
FIG. 7 illustrates an alternate embodiment of what is depicted in FIG. 6.

In some embodiments according to the present technology, referring now to FIG. 7, the mandrel 700 has an inner core 704 that is tapered for ease of insertion and extraction, where the fully inserted core 704 provides outward mechanical force on the mandrel outer portion to maintain substantial friction and support against the inner wall of the polymer tube 200. The mandrel inner core 704 may be metal, glass, or an arbitrary material since cross-contamination is prevented by the mandrel outer portion serving as a barrier layer.

The laser for ablative machining may include an ultrafast laser source to achieve athermal material removal by way of ionization and Coulomb explosion rather than thermal deposit and melting.

A three-jaw chuck may be used to advance and rotate the tube/mandrel assembly for machining. The rigid inner mandrel core may be supplied within the tube as it is fed into the beam path, or it may be inserted into an open end of the tube/mandrel from the direction opposite the tube stock feed. Thus the inner core pin insertion mechanism may be added to existing tube cutting workstations with minimal rework.

The inner core element 704 may, in fact, be high-pressure gas instead of a solid pin. The gas pressure provides similar outward pressure as would the tapered pin, with the advantage here being instant, low force removal of the "core" simply by gas pressure release.

Figure 8:
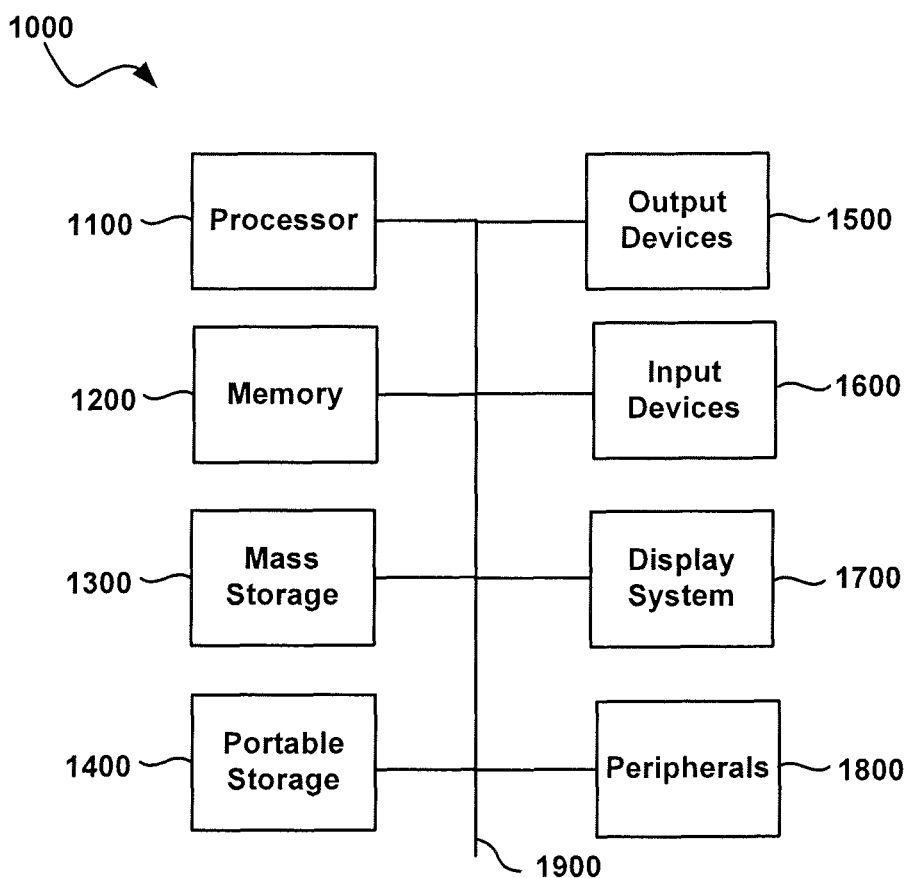
FIG. 8 illustrates an exemplary computer system that may be used with certain embodiments according to the present technology.

FIG. 8 illustrates an exemplary computing system 1000 that may be used to implement an embodiment of the present technology. The system 1000 of FIG. 8 may be implemented in the contexts of the likes of computing systems, networks, servers, or combinations thereof. The computing system 1000 of FIG. 8 includes one or more processors 1100 and main memory 1200. Main memory 1200 stores, in part, instructions and data for execution by processor 1100. Main memory 1200 may store the executable code when in operation. The system 1000 of FIG. 8 further includes a mass storage device 1300, portable storage medium drive(s) 1400, output devices 1500, user input devices 1600, a graphics display 1700, and peripheral devices 1800.

The components shown in FIG. 8 are depicted as being connected via a single bus 1900. The components may be connected through one or more data transport means. Processor unit 1100 and main memory 1200 may be connected via a local microprocessor bus, and the mass storage device 1300, peripheral device(s) 1800, portable storage device 1400, and display system 1700 may be connected via one or more input/output (I/O) buses.

Mass storage device 1300, which may be implemented with a magnetic disk drive or an optical disk drive, is a non-volatile storage device for storing data and instructions for use by processor unit 1100. Mass storage device 1300 may store the system software for implementing embodiments of the present invention for purposes of loading that software into main memory 1200.

Portable storage device 1400 operates in conjunction with a portable non-volatile storage medium, such as a floppy disk, compact disk, digital video disc, or USB storage device, to input and output data and code to and from the computer system 1000 of FIG. 8. The system software for implementing embodiments of the present invention may be stored on such a portable medium and input to the computer system 1000 via the portable storage device 1400.

Input devices 1600 provide a portion of a user interface. Input devices 1600 may include an alphanumeric keypad, such as a keyboard, for inputting alpha-numeric and other information, or a pointing device, such as a mouse, a trackball, stylus, or cursor direction keys. Additionally, the system 1000 as shown in FIG. 8 includes output devices 1500. Suitable output devices include speakers, printers, network interfaces, and monitors.

Display system 1700 may include a liquid crystal display (LCD) or other suitable display device. Display system 1700 receives textual and graphical information, and processes the information for output to the display device.

Peripherals 1800 may include any type of computer support device to add additional functionality to the computer system. Peripheral device(s) 1800 may include a modem or a router.

The components provided in the computer system 1000 of FIG. 8 are those typically found in computer systems that may be suitable for use with embodiments of the present invention and are intended to represent a broad category of such computer components that are well known in the art. Thus, the computer system 1000 of FIG. 8 may be a personal computer, hand held computing system, telephone, mobile computing system, workstation, server, minicomputer, mainframe computer, or any other computing system. The computer may also include different bus configurations, networked platforms, multi-processor platforms, etc. Various operating systems may be used including Unix, Linux, Windows, Macintosh OS, Palm OS, Android, iPhone OS and other suitable operating systems.

It is noteworthy that any hardware platform suitable for performing the processing described herein is suitable for use with the technology. Computer-readable storage media refer to any medium or media that participate in providing instructions to a central processing unit (CPU), a processor, a microcontroller, or the like. Such media may take forms including, but not limited to, non-volatile and volatile media such as optical or magnetic disks and dynamic memory, respectively. Common forms of computer-readable storage media include a floppy disk, a flexible disk, a hard disk, magnetic tape, any other magnetic storage medium, a CD-ROM disk, digital video disk (DVD), any other optical storage medium, RAM, PROM, EPROM, a FLASHEPROM, any other memory chip or cartridge.

The present technology is described above with reference to example embodiments. It will be apparent to those skilled in the art that various modifications may be made and other embodiments can be used without departing from the broader scope of the present technology. For example, the "tube" may be something other than a stent, and may be made of a material other than a polymer. Therefore, these and other variations upon the exemplary embodiments are intended to be covered by the present technology.

What is claimed is:

1. An apparatus for athermal ablation of a workpiece, the apparatus comprising:
   a laser device to direct a laser beam at the workpiece to remove a plurality of sections from the workpiece by the athermal ablation, the removal occurring in a plurality of discrete motions that cause the laser beam to trace along outer perimeters of the plurality of sections in a specific order so as to maintain mechanical stability of the plurality of sections, wherein a frequency of the laser beam causes the athermal ablation at the workpiece, wherein the discrete motions include multiple lead-ins and lead-outs away from the perimeters of the plurality of sections; and
   a workpiece holder to hold and maneuver the workpiece during the removal of the plurality of sections.

2. The apparatus of claim 1, wherein the workpiece holder includes one or more polymer materials.

3. The apparatus of claim 1, wherein the workpiece holder is configured to hold a hollow tube.

4. The apparatus of claim 3, wherein the workpiece holder includes a mandrel to support the workpiece from the inside of the workpiece during the ablation process.

5. The apparatus of claim 4, wherein the mandrel includes at least an outer layer composed of the same material as the workpiece.

6. The apparatus of claim 4, wherein the mandrel is pressurized with a gas to increase and decrease the size of the mandrel in order to grip and release the workpiece.

7. The apparatus of claim 4, wherein the mandrel includes a spring loaded mechanism to grip and release the workpiece.

8. The apparatus of claim 4, wherein the mandrel includes an inner core that is tapered for ease of insertion and extraction.

9. The apparatus of claim 4, wherein a mandrel inner core includes a metal or a glass.

10. The apparatus of claim 1, wherein the workpiece holder is configured to hold a substantially flat workpiece.

11. The apparatus of claim 1, wherein the laser beam is generated by an ultrafast laser.

12. The apparatus of claim 1, wherein parameters of the laser beam are dynamically adjustable.

13. The apparatus of claim 1, wherein the laser device is configured to maneuver the laser beam in operation.

14. The apparatus of claim 1, further comprising a computer system having computer executable instructions configured to remove the plurality of sections that are selected in such a way that the workpiece is moved around its axis substantially in one direction as to avoid torsional distortion.

15. The apparatus of claim 1, wherein the workpiece holder is configured to hold a tubing structure including one or more of the following medical devices: an intravascular stent, a tumor encapsulator, and a catheter.

16. The apparatus of claim 1, further comprising a computer system having computer executable instructions configured to remove the plurality of sections using a multi-pass cutting technique, the workpiece being repetitively moved below the laser beam so that the laser beam traces outer perimeters of the plurality of sections for a plurality of passes, each pass cutting a partial thickness of the workpiece being machined away by the laser beam until a sufficient number of passes results in the laser beam cutting through the workpiece.

17. The apparatus of claim 1, further comprising a process gas nozzle, which is of a tapered conical shape with a small orifice positioned above a focal point of the laser beam, a clearance notch being cut into a side of the process gas nozzle to permit closer proximity to the focal point and to improve positioning stability of the workpiece.

18. The apparatus of claim 1, further comprising a computer system having computer executable instructions configured to make the laser beam cut a part of a section by starting in a first location internal to the section, moving onto the outer perimeter of the section, cutting along the outer perimeter of the section, and moving to a second location internal to the section.

19. The apparatus of claim 18, wherein the computer executable instructions are configured to remove the section by skipping parts of the outer perimeter of the section as to maintain mechanical stability of the section.

20. The apparatus of claim 1, wherein the laser beam is to achieve athermal material removal by ionization and Coulomb explosion.

21. The apparatus of claim 1, further comprising a process gas nozzle to deliver process gas substantially coaxially with the laser beam, the process gas clearing debris resulting from the laser ablation of the workpiece.

\* \* \* \* \*